United States Patent
Burkoth et al.

(10) Patent No.: US 8,772,255 B2
(45) Date of Patent: Jul. 8, 2014

(54) CELL TRANSFECTING FORMULATIONS OF SMALL INTERFERING RNA RELATED COMPOSITIONS AND METHODS OF MAKING AND USE

(75) Inventors: Timothy S. Burkoth, San Francisco, CA (US); Anne B. Jefferson, Oakland, CA (US); Christoph Reinhard, Alameda, CA (US); Ronald N. Zuckermann, El Cerrito, CA (US)

(73) Assignee: Novartis Vaccines and Diagnostics, Inc., Cambridge, MA (US)

(*) Notice: Subject to any disclaimer, the term of this patent is extended or adjusted under 35 U.S.C. 154(b) by 319 days.

(21) Appl. No.: 12/053,486

(22) Filed: Mar. 21, 2008

(65) Prior Publication Data

US 2009/0143322 A1 Jun. 4, 2009

Related U.S. Application Data

(62) Division of application No. 11/018,888, filed on Dec. 20, 2004, now abandoned.

(60) Provisional application No. 60/530,953, filed on Dec. 19, 2003.

(51) Int. Cl.
*C12N 15/113* (2010.01)
*A61K 47/48* (2006.01)

(52) U.S. Cl.
CPC .............. *C12N 15/113* (2013.01); *A61K 47/48* (2013.01)
USPC ........................................ 514/44 A; 514/773

(58) Field of Classification Search
None
See application file for complete search history.

(56) References Cited

U.S. PATENT DOCUMENTS

| | | |
|---|---|---|
| 6,197,332 B1 | 3/2001 | Zuckermann et al. |
| 6,569,450 B1 | 5/2003 | Zuckermann et al. |
| 6,572,881 B1 | 6/2003 | Zuckermann et al. |
| 6,677,445 B1 | 1/2004 | Innis et al. |
| 2006/0019912 A1 | 1/2006 | Burkoth et al. |

FOREIGN PATENT DOCUMENTS

| | | |
|---|---|---|
| WO | WO 99/08711 | 2/1999 |
| WO | WO 01/16306 | 3/2001 |
| WO | WO 2005/007196 | 1/2005 |
| WO | WO 2005/060697 | 7/2005 |

OTHER PUBLICATIONS

Agami, "RNAi and related Mechanisms and Their Potential Use for Therapy" Current Opinion in Chemical Bioloqy 6:829-834, 2002.
Agrawal et. al., "Antisense Therapeutics: is it as Simple as Complementary Base Recognition?" Molecular Medicine Today 6:72-81, Feb. 2000.
Caplen, "RNAi as a Gene Therapy Approach" Experimental Opinion in Biological Therapeutics 3: 575-586, 2003.
Cheng, Richard P. et al., β-Peptides: From Structure to Function, Chemical Reviews, 2001, vol. 101, No. 10, p. 3219-3232.
Coburn and Cullen, 'siRNAs: a New Wave of RNA-Based Therapeutics J. Animicrobial Chemotherapy 51:753-756, 2003.
Elbashir et.al., "Duplexes of 21-Nucleotides RNAs Mediate RNA Interference in Cultured Mammalian Cells" Nature 411:494-498, May 2001.
Harborth, Jens et al., Identification of essential genes in cultured mammalian cells using small interfering RNAs, Journal Of Cell Science 114 (24), pp. 4557-4565.
Jen et.al. &., "Suppression of Gene Expression by Targeted Disruption of Messenger RNA: Available Options and Current Strategies" Stem Cells 18:307-319, 2000.
Lobo et.al., "Structure/Function Analysis of Peptoid/Liptod: DNA Complexes" J. Pharmaceutical Sciences 92 (9):1905-1918, Sep. 2003.
Vickers et. al. Journal of Biological Chemistry 2003, vol. 278, pp. 7108-7118.
PCT International Search Report dated Feb. 7, 2006 issued in PCT/US2004/042911.
PCT International Preliminary Report on Patentability and Written Opinion dated Jun. 20, 2006 issued in PCT/US2004/042911.
EP Supplementary Search Report dated Dec. 1, 2009 issued in EP 04 815 034.6-1223.
Murphy et al. (1998) "A combinatorial approach to the discovery of efficient cationic peptoid reagents for gene deliver" *Proceeding of the National Academy of Science of USA*, National Academy of Science 95(4):1517-1522.
Utku et al. (2006) "A peptidomimetic siRNA transfection reagent for highly effective gene silencing" *Molecular BioSystems* 2(6-7):312-317.

*Primary Examiner* — Tracy Vivlemore
(74) *Attorney, Agent, or Firm* — Jennifer Wahlsten; Helen Lee

(57) ABSTRACT

Compositions incorporating small interfering ribonucleic acid (siRNA) and certain lipid-conjugated polyamide compound-based delivery vehicles that are particularly useful in the delivery siRNA and other polynucleotides to cells. Also, methods of making and using the compositions.

8 Claims, 3 Drawing Sheets

CELL TRANSFECTING FORMULATIONS OF SMALL INTERFERING RNA RELATED COMPOSITIONS AND METHODS OF MAKING AND USE

CROSS-REFERENCE TO RELATED APPLICATIONS

This application is a divisional of U.S. application Ser. No. 11/018,888, filed Dec. 20, 2004 now abandoned; which claims the benefit of U.S. Provisional Application No. 60/530,953, filed Dec. 19, 2003, the disclosures of each of which are hereby incorporated herein in their entirety.

SEQUENCE LISTING

The instant application contains a Sequence Listing which has been submitted electronically in ASCII format and is hereby incorporated by reference in its entirety. Said ASCII copy, created on Apr. 25, 2014, is named NOVDP019D1_seqlist.txt and is 996 bytes in size.

FIELD OF THE INVENTION

This invention relates to compositions incorporating small interfering ribonucleic acid (siRNA) with lipid-conjugated polyamide compounds, methods for making them, as well as methods for their use in the delivery of siRNA to cells. The invention also relates to a novel class of lipid-conjugated polyamide compounds suitable for use in the delivery of polynucleotides, including siRNA, to cells

BACKGROUND OF THE INVENTION

RNA interference refers to the phenomenon of the presence of double stranded RNA in a cell eliminating the expression of a gene having the same sequence, while leaving the expression of other unrelated genes undisturbed. This phenomenon, also known as "post transcriptional gene silencing" or "RNA silencing" has been noted in plants for some time, but has only more recently been recognized in animals. Fire et al., Nature, 391, 806 (1998). The discovery of this functionality suggests the possibility of powerful research tools for stopping the production of a specific protein and gene-specific therapeutics operating by this mechanism.

Details of the RNA interference (RNAi) mechanism have recently been elucidated. The presence of long dsRNAs in cells stimulates the activity of a ribonuclease III enzyme known to as Dicer. Dicer is involved in the processing of the dsRNA into short pieces of dsRNA known as small interfering RNAs (siRNA) (Berstein et al., Nature, 409, 363 (2001)). Small interfering RNAs derived from Dicer activity are typically about 21-23 nucleotides in length. The RNAi response also features an endonuclease complex containing an siRNA, commonly referred to as an RNA-induced silencing complex (RISC). The RISC complex mediates cleavage of single stranded RNA having sequence complementary to the antisense strand of the siRNA duplex. Cleavage of the target RNA takes place in the middle of the region complementary to the antisense strand of the siRNA duplex. Elbashir et al., Genes Dev., 15, 188 (2001).

One potential impediment to harnessing the RNAi phenomenon in mammalian cells is that the presence of long dsRNAs in these cells also stimulates an interferon response that results in non-specific cleavage of mRNA by a ribonuclease. However, it has been shown that chemically synthesized 21-meric small interfering RNAs (siRNAs) effectively suppress gene expression in several human cell lines without eliciting an interferon response. Elbashir et al., Nature, 411, 494 (2001). In particular, synthetic siRNAs have been found to be most active when containing 21 nucleotide duplexes with two TT nucleotide 3'-overhangs. Elbashir et al., EMBO J., 20, 6877 (2001).

SiRNA's characteristics of high specificity, resistance to ribonucleases, non-immunogenicity and potency suggest tremendous potential as a cell transfection agent for research and therapeutic applications. A variety of strategies exist for delivery of nucleic acid compositions to cells. However, technical difficulties have been encountered in transfecting siRNA into cells. Viral vectors provide relatively efficient delivery, but in some cases present safety problems due to the risk of immunological complications or unwanted propagation in the subject. Adenoviral vectors have shown certain advantages in that they do not integrate into the genome of the cell and can be transduced into resting cells. However, all of these vectors must be prepared by time-consuming recombinant DNA techniques. Oligonucleotides may also be delivered to cells via chemical transfection agents, which have been the subject of much recent work. These agents include polycationic molecules, such as polylysine, and cationic lipids. The liposomal composition Lipofectin® (Felgner et al., PNAS 84:7413, 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. Other methods, such as calcium phosphate mediated transfection, can be used to deliver the oligonucleotides to cells according to reported procedures. However, there is a need for effective, nontoxic siRNA transfection agents that are easy to use and applicable to many cell types.

SUMMARY OF THE INVENTION

To achieve the foregoing, the present invention provides compositions incorporating small interfering ribonucleic acid (siRNA) and certain lipid-conjugated polyamide compound-based delivery vehicles that are particularly useful in the delivery of polynucleotides, including siRNA, to cells.

In one aspect, the invention provides compositions incorporating small interfering ribonucleic acid (siRNA) and lipid-conjugated polyamide compounds having the general formula:

$$R_a-[(NR_1-W-CO)_n]_m-R_c \qquad (I)$$

wherein n is an integer selected from 1 to about 48 and m is an integer selected from about 2 to about 48, wherein $R_1$ for each monomeric unit, —(NR$_1$—W—CO)—, and $R_a$ are independently selected from the group consisting of a hydrogen atom; a hydroxy group; an amino group; a carboxyl group; a sulfonyl group; —SH; an optionally substituted, branched or straight chain aliphatic group having 1 to 8 carbon atoms in a backbone structure that optionally contains nitrogen, oxygen, sulfur, and phosphorus, wherein said aliphatic group optionally has one or more double or triple bonds; an optionally substituted aryl group having 3 to 12 carbon atoms in a backbone structure that optionally contains nitrogen, oxygen, sulfur, and phosphorus; an optionally substituted arylalkyl group having 3 to 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to linker moiety, wherein $R_1$ is not a hydrogen atom for at least one monomeric unit, wherein $R_c$ is selected from a hydrogen atom; a hydroxy group; an amino group; a hydrazine group; a sulfonyl group; —SH; an optionally substituted, branched or straight chain aliphatic group having 1 to 8 carbon atoms in a backbone structure that optionally contains nitrogen, oxygen, sulfur, and phosphorus, wherein said aliphatic group optionally has one or more double or triple bonds; an optionally substituted aryl group having 3 to 12 carbon atoms in a backbone structure that optionally contains nitrogen, oxygen, sulfur, and phosphorus; an optionally substituted arylalkyl group having 3 to 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to a linker moiety, wherein when $R_1$, $R_a$, or $R_c$ is an aryl or arylalkyl group having fewer than 5 carbon atoms in a backbone structure, said backbone structure further comprises one or more oxygen and/or nitrogen atoms, wherein W for each monomeric unit is independently selected from an optionally substituted, branched or straight chain divalent moiety having from 1 to about 50 atoms and optionally, one or more double or triple bonds in a backbone that contains carbon and optionally contains nitrogen, oxygen, sulfur, and phosphorus, wherein said optional substitution of W may be a lipid moiety that is optionally bonded to a linker moiety, wherein said lipid moiety is a hydrophobic or amphipathic moiety selected from the group consisting of:

(i) optionally substituted aryl or arylalkyl moieties having from about 14 to about 50 carbon atoms in a backbone structure that optionally contains nitrogen, oxygen, sulfur, and phosphorus, wherein the alkyl group of said arylalkyl optionally has one or more double or triple bonds; and (ii) optionally substituted, branched or straight chain aliphatic moieties having from about 10 to about 50 carbon atoms in a backbone structure that optionally contains nitrogen, oxygen, sulfur, and phosphorus, wherein said aliphatic moieties optionally have one or more double or triple bonds, and wherein at least one of $R_a$, $R_c$, W for a single monomeric unit and $R_1$ for a single monomeric unit comprises a lipid moiety.

In a particular embodiment, the invention provides a composition including a siRNA in a pharmaceutically acceptable vehicle. The composition may be useful for delivering the siRNA to a cell, in vitro or in vivo, to inhibit expression of a gene of interest. The vehicle includes one or more lipid-cationic peptoid conjugates of the formula:

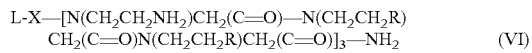

and positional isomers
where

L is selected from a non-steroidal lipid moiety comprising at least one fatty alkyl or alkenyl chain between about 8 and 24 carbon atoms in length, and a sterol moiety;

each group R is independently selected from alkyl, aminoalkyl, and aralkyl, and

X is selected from the group consisting of a direct bond, an oligopeptide, a substantially linear alkyl chain from 2 to about 30 bonds in length, and a substantially linear chain from 2 to about 30 bonds in length consisting of alkyl bonds and one or more linkages selected from the group consisting of ester, amide, carbonate, carbamate, disulfide, peptide, and ether.

When L is a non-sterol lipid moiety (that is, a lipid moiety that is not or does not contain a sterol group, such as a phospholipid group (i.e., ROOCCH$_2$CH(COOR)CH$_2$OP(O)$_2$O—), the lipid-cationic polyamide conjugate is referred to herein as a "lipitoid." When L is a sterol moiety, (that is, a lipid moiety that is or contains a sterol group, such as a cholesterol group), the lipid-cationic polyamide conjugate is referred to herein as a "cholesteroid." The lipid-cationic peptoid conjugate in a composition of the present invention may be a lipitoid, a cholesteroid, or, in one important embodiment, a combination thereof.

In specific embodiments, R is isopropyl or 4-methoxyphenyl. A single lipitoid or cholesteroid may include different groups R, or they may be the same within the molecule.

The compositions of the invention result in efficient delivery of the biologically active siRNA to mammalian cells effective to knockout the mRNA of a target gene.

In another aspect, a method of inhibiting expression of a target gene in a subject, which involves administering to the subject a composition as described above, in which one strand of the siRNA duplex has a nucleotide sequence comprised in a mRNA derived from the target gene is provided. In a specific embodiment, a strand of the siRNA duplex includes a sequence represented by SEQ ID NO: 1, disclosed herein, and the target gene/mRNA is Akt1.

In another aspect, the invention provides a polynucleotide delivery vehicle composed of a mixture of at least one lipitoid and one cholesteroid. This combination lipitoid/cholesteroid delivery vehicle is suitable for delivery of a variety of polynucleotides such as plasmid DNA, antisense oligonucleotides and siRNA, to cells in compositions incorporating such polynucleotides and the combination lipitoid/cholesteroid delivery vehicle.

Methods of manufacturing compounds and compositions described herein are provided and contemplated to fall within the scope of the invention as is the use of the compositions in methods for manufacturing medicaments for use in the methods of the invention.

These and other objects and features of the invention will become more fully apparent when the following detailed description of the invention is read in conjunction with the accompanying drawings.

DESCRIPTION OF SPECIFIC EMBODIMENTS OF THE INVENTION

Figure 1:
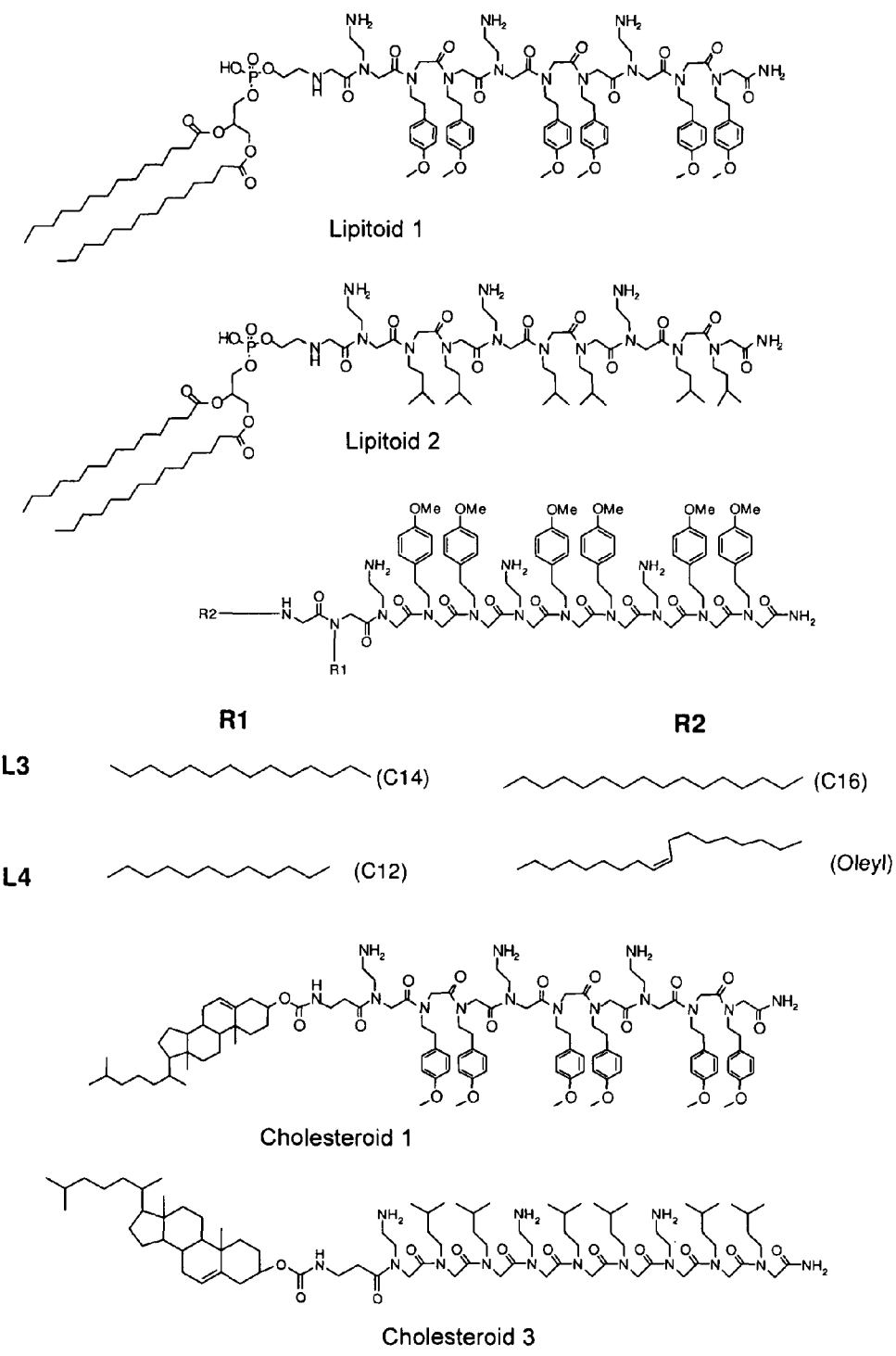
FIG. 1 shows a selection of lipid-cationic peptoid conjugates ("lipitoids" and "cholesteroids") useful as siRNA carriers in compositions and methods of the invention.

The materials and associated techniques and apparatuses of the present invention will now be described with reference to several embodiments. Important properties and characteristics of the described embodiments are illustrated in the structures in the text. While the invention will be described in conjunction with these embodiments, it should be understood that the invention it is not intended to be limited to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Introduction

The present invention provides compositions incorporating small interfering ribonucleic acid (siRNA) and lipid-conjugated polyamide-based delivery vehicles that are particularly useful in the delivery of siRNA to cells. In another aspect, the invention provides a polynucleotide delivery vehicle composed of a mixture of at least one lipitoid and one cholesteroid. The delivery vehicle is suitable for delivery of a variety of polynucleotides, such as plasmid DNA, antisense oligonucleotides and siRNA, to cells.

In one aspect, the invention provides compositions incorporating small interfering ribonucleic acid (siRNA) and lipid-conjugated polyamide compounds having the general formula:

$$R_a\text{—}[(NR_1\text{—}W\text{—}CO)_n]_m\text{—}R_c \qquad (I)$$

wherein n is an integer selected from 1 to about 48 and m is an integer selected from about 2 to about 48, wherein $R_1$ for each monomeric unit, —($NR_1$—W—CO)—, and $R_a$ are independently selected from the group consisting of a hydrogen atom; a hydroxy group; an amino group; a carboxyl group; a sulfonyl group; —SH; an optionally substituted, branched or straight chain aliphatic group having 1 to 8 carbon atoms in a backbone structure that optionally contains nitrogen, oxygen, sulfur, and phosphorus, wherein said aliphatic group optionally has one or more double or triple bonds; an optionally substituted aryl group having 3 to 12 carbon atoms in a backbone structure that optionally contains nitrogen, oxygen, sulfur, and phosphorus; an optionally substituted arylalkyl group having 3 to 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to a linker moiety, wherein $R_1$ is not a hydrogen atom for at least one monomeric unit, wherein $R_c$ is selected from a hydrogen atom; a hydroxy group; an amino group; a hydrazine group; a sulfonyl group; —SH; an optionally substituted, branched or straight chain aliphatic group having 1 to 8 carbon atoms in a backbone structure that optionally contains nitrogen, oxygen, sulfur, and phosphorus, wherein said aliphatic group optionally has one or more double or triple bonds; an optionally substituted aryl group having 3 to 12 carbon atoms in a backbone structure that optionally contains nitrogen, oxygen, sulfur, and phosphorus; an optionally substituted arylalkyl group having 3 to 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to a linker moiety, wherein when $R_1$, $R_a$, or $R_c$ is an aryl or arylalkyl group having fewer than 5 carbon atoms in a backbone structure, said backbone structure further comprises one or more oxygen and/or nitrogen atoms, wherein W for each monomeric unit is independently selected from an optionally substituted, branched or straight chain divalent moiety having from 1 to about 50 atoms and optionally, one or more double or triple bonds in a backbone that contains carbon and optionally contains nitrogen, oxygen, sulfur, and phosphorus, wherein said optional substitution of W may be a lipid moiety that is optionally bonded to a linker moiety, wherein said lipid moiety is a hydrophobic or amphipathic moiety selected from the group consisting of:

(i) optionally substituted aryl or arylalkyl moieties having from about 14 to about 50 carbon atoms in a backbone structure that optionally contains nitrogen, oxygen, sulfur, and phosphorus, wherein the alkyl group of said arylalkyl optionally has one or more double or triple bonds; and (ii) optionally substituted, branched or straight chain aliphatic moieties having from about 10 to about 50 carbon atoms in a backbone structure that optionally contains nitrogen, oxygen, sulfur, and phosphorus, wherein said aliphatic moieties optionally have one or more double or triple bonds, and wherein at least one of $R_a$, $R_c$, W for a single monomeric unit and $R_1$ for a single monomeric unit comprises a lipid moiety.

In a particular embodiment, the invention provides a composition including a siRNA in a pharmaceutically acceptable vehicle. The composition may be useful for delivering the siRNA to a cell, in vitro or in vivo, to inhibit expression of a gene of interest. The vehicle includes one or more lipid-cationic peptoid conjugates of the formula:

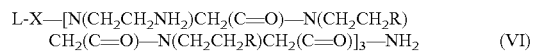

$$\text{L-X—[N(CH}_2\text{CH}_2\text{NH}_2\text{)CH}_2\text{(C}\!=\!\text{O)—N(CH}_2\text{CH}_2\text{R)} \\ \text{CH}_2\text{(C}\!=\!\text{O)—N(CH}_2\text{CH}_2\text{R)CH}_2\text{(C}\!=\!\text{O)]}_3\text{—NH}_2 \qquad (VI)$$

and positional isomers
where

L is selected from a non-steroidal lipid moiety comprising at least one fatty alkyl or alkenyl chain between about 8 and 24 carbon atoms in length, and a sterol moiety;

each group R is independently selected from alkyl, aminoalkyl, and aralkyl, and

X is selected from the group consisting of a direct bond, an oligopeptide, a substantially linear alkyl chain from 2 to about 30 bonds in length, and a substantially linear chain from 2 to about 30 bonds in length consisting of alkyl bonds and one or more linkages selected from the group consisting of ester, amide, carbonate, carbamate, disulfide, peptide, and ether.

When L is a non-sterol lipid moiety (that is, a lipid moiety that is not or does not contain a sterol group, such as a phospholipid group (i.e., $ROOCCH_2CH(COOR)CH_2OP(O)_2O$—), the lipid-cationic polyamide conjugate is referred to herein as a "lipitoid." When L is a sterol moiety, (that is, a lipid moiety that is or does contain a sterol group, such as a cholesterol group), the lipid-cationic polyamide conjugate is referred to herein as a "choiesteroid." The lipid-cationic polyamide conjugate in a composition of the present invention may be a lipitoid, a cholesteroid, or, in one important embodiment, a combination thereof.

In specific embodiments, R is isopropyl or 4-methoxyphenyl. A single lipitoid or cholesteroid may include different groups R, or they may be the same within the molecule.

The compositions of the invention result in efficient delivery of siRNA to mammalian cells effective to knockout the mRNA of a target gene.

In another aspect, a method of inhibiting expression of a target gene in a subject, which involves administering to the subject a composition as described above, in which one strand of the siRNA duplex has a nucleotide sequence comprised in a mRNA derived from the target gene is provided. In another embodiment a method of manufacturing a composition as described above for use in inhibiting expression of a target gene in a subject is provided. In a specific embodiment, a strand of the siRNA duplex includes a sequence represented by SEQ ID NO: 1, disclosed herein, with two nucleotide 3'-overhangs and phosphodiester links throughout, may be used, and the target gene/mRNA is Akt1.

In another aspect, the invention provides a polynucleotide delivery vehicle composed of a mixture of at least one lipitoid and one cholesteroid. The combination lipitoid/cholesteroid delivery vehicle is suitable for delivery of a variety of polynucleotides such as plasmid DNA, antisense oligonucleotides and siRNA, to cells in compositions incorporating such polynucleotides and the combination lipitoid/cholesteroid delivery vehicle.

Compositions and delivery vehicles in accordance with the present invention may be used in vitro, for example in connection with research including drug discovery, development and testing activities, or in vivo for therapeutic applications (e.g., as drugs of drug components for treating disease) in animal, including mammalian (e.g., human) subjects. For such in vivo applications, a pharmaceutically acceptable vehicle in accordance with the present invention is used.

Definitions

Unless otherwise noted, terminology used herein should be given its normal meaning as understood by one of skill in the art. In order to facilitate understanding of the present invention, a number of defined terms are used herein to designate particular elements of the present invention. When so used, the following meanings are intended:

The term "lipid-conjugated polyamide" is used herein to refer to a compound having both an oligomeric amide moiety and one or more lipid moieties. The polyamide component of the lipid-conjugated polyamide compound may, for example, be a peptoid, in which case the lipid-conjugated polyamide may be referred to as a "lipid-conjugated peptoid," in particular a cationic peptoid, in which case the lipid-conjugated polyamide may be referred to as a "lipid-cationic peptoid conjugate."

As used herein, the term "lipid" refers to a hydrophobic or amphipathic moiety. A lipid moiety can be conjugated directly to the oligomeric amide moiety, or optionally, indirectly to the oligomeric amide moiety via a linker moiety. The lipid component of the lipid-conjugated polyamide may be or contain a non-sterol or a sterol moiety.

As used herein, the term "lipitoid" refers to a lipid-conjugated peptoid of the formula:

L-X—[N(CH$_2$CH$_2$NH$_2$)CH$_2$(C=O)—N(CH$_2$CH$_2$R)CH$_2$(C=O)—N(CH$_2$CH$_2$R)CH$_2$(C=O)]$_3$—NH$_2$    (VI)

wherein the lipid portion, L, is a non-sterol lipid moiety. Wherever used in the specification and claims herein, it is intended that this formula cover positional isomers or the peptoid portion thereof, a positional isomer being any repeating three-fold motif of the peptoid portion of the formula.

As used herein, the term "cholesteroid" refers to a lipid-conjugated peptoid of the formula:

L-X—[N(CH$_2$CH$_2$NH$_2$)CH$_2$(C=O)—N(CH$_2$CH$_2$R)CH$_2$(C=O)N(CH$_2$CH$_2$R)CH$_2$(C=O)]$_3$—NH$_2$ wherein the lipid portion, L, is a sterol lipid moiety. Wherever used in the specification and claims herein, it is intended that this formula cover positional isomers or the peptoid portion thereof, a positional isomer being any repeating three-fold motif of the peptoid portion of the formula.

The terms "oligomeric" and "oligomeric amide" are used interchangeably herein to refer to two or more monomer units that are linked together by an amide bond, i.e., —[—(NR$_1$—W—CO)$_n$]$_m$—.

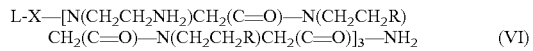

As used herein, the term "monomer" or "monomeric" unit refers to the unit defined by the formula

—(NR$_1$—W—CO)—.

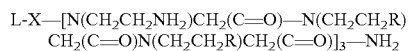

The terms "oligomeric reactant," "oligomer reactant," "oligomeric amide reactant," and "lipid reactant" refer herein to reactive species from which lipid-conjugated polyamide compounds of the present invention are synthesized.

As used herein, the term "delivery vehicle" refers to a lipid-conjugated polyamide compound as further described herein that complexes with and facilitates the delivery of a polynucleotide through a cell membrane to a target site. Delivery vehicles in accordance with the present invention are "pharmaceutically acceptable," which, as used herein, refers to the compatibility of the delivery vehicles with biological materials, for example, for use in pharmaceutical formulations and in other applications, either in vivo or in vitro, where they are in contact with biological materials, such as living cells.

As used herein, the term "complex" refers to a structure formed by interaction between two or more compounds or structures. Such interaction can be via chemical interaction, such as, for example, covalent, ionic, or secondary bonding (e.g., hydrogen bonding), and the like, or via physical interaction, such as, for example, encapsulation, entrapment, and the like.

In accordance with one aspect of the present invention, lipid-conjugated polyamide compounds may be complexed to siRNA via covalent bonding through an intermediately positioned sequence of amino acids that is susceptible to degradation by endogenous proteolytic enzymes. Thus, for example, exposure of the complex to degradative enzymes results in cleavage and subsequent release of the siRNA from the complex. Lipid-conjugated polyamide compounds of the present invention can also be complexed to siRNA via ionic or secondary bonding, or alternatively via encapsulation or entrapment.

The terms "polynucleotide" and "polynucleic acid" are used interchangeably herein to refer to DNA, RNA, and analogues thereof peptide-nucleic acids, as well as, DNA or RNA that has non-phosphate containing nucleotides. SiRNA is particularly used in accordance with the present invention. Other polynucleotides employed in the practice of some aspects of the present invention can be single-stranded, double-stranded, or chimeric single- or double-stranded molecules. Specific examples include plasmid DNA and antisense oligonucleotides.

As used herein, "substituted" is meant that one or more pendant hydrogen's on an organic functional group is replaced with a substituent, preferably selected from a halide, a lower alkyl or lower alkoxy group, halomethyl, or haloethyl.

All publications mentioned herein are incorporated herein by reference for the purpose of disclosing and describing features of the invention for which the publications are cited in connection with.

Compositions

In one aspects, the present invention provides compositions incorporating small interfering ribonucleic acid (siRNA) and lipid-conjugated polyamide based delivery vehicles. These compositions are particularly useful in the delivery of the siRNA to cells.

1. SiRNA

The compositions of the present invention incorporate siR-NAs which are effective to specifically suppress expression of a gene of interest without eliciting any other activity detrimental to normal cell function, e.g., an interferon response. Effective siRNAs are generally, but not necessarily, chemically synthesized. In specific embodiments, siRNA directed against Akt1 messenger RNA having the sequence CAUAGUGAGGUUGCAUCUGGUG (SEQ ID No: 1) with two nucleotide 3'-overhangs and phosphodiester links throughout may be used. In one case, the two nucleotide 3'-overhangs are TT (DNA) nucleotides. In another case, the two nucleotide 3'-overhangs are 2' O-methyl UU (RNA) nucleotides.

When transfected into cells, as described in Examples 1 and 3, below, these siRNA showed very effective degradation of endogenous Akt1 mRNA, resulting in a loss of activity of the corresponding Akt1 gene. It should be understood that the Akt1 siRNA sequences described herein are merely representative of a myriad other possible siRNA sequences that may be combined with lipid-conjugated polyamide compound delivery vehicles in compositions in accordance with the present invention. One of skill in the art will appreciate for the disclosure provided herein that other siRNA sequences may be used in the same or a similar readily ascertainable manner to achieve the same effect for the corresponding mRNA and gene.

2. Lipid-Conjugated Polyamide Compounds

The present invention provides compositions incorporating lipid-conjugated polyamide compound-based delivery vehicles. Suitable lipid-conjugated polyamide conjugates for use in or as these delivery vehicles are described in co-owned PCT publications WO 98/06437 and WO 99/08711 (Zuckermann et al.), based on U.S. Ser. Nos. 60/023,867, 60/054,743, and 09/132,808; and in co-owned PCT publication WO 01/16306 and U.S. Ser. No. 09/648,254 (Innis, et al.), based on U.S. Ser. No. 60/151,246; hereby incorporated by reference in their entirety and for all purposes. These lipid-conjugated polyamide conjugates have the general formula:

$$R_a\text{-}[(NR_1\text{—}W\text{—}CO)_n]_m\text{—}R_c \qquad (I)$$

wherein n is an integer selected from 1 to about 48 and m is an integer selected from about 2 to about 48, wherein $R_1$ for each monomeric unit, —(NR$_1$—W—CO)—, and $R_a$ are independently selected from the group consisting of a hydrogen atom; a hydroxy group; an amino group; a carboxyl group; a sulfonyl group; —SH; an optionally substituted, branched or straight chain aliphatic group having 1 to 8 carbon atoms in a backbone structure that optionally contains nitrogen, oxygen, sulfur, and phosphorus, wherein said aliphatic group optionally has one or more double or triple bonds; an optionally substituted aryl group having 3 to 12 carbon atoms in a backbone structure that optionally contains nitrogen, oxygen, sulfur, and phosphorus; an optionally substituted arylalkyl group having 3 to 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to linker moiety, wherein $R_1$ is not a hydrogen atom for at least one monomeric unit, wherein $R_c$ is selected from a hydrogen atom; a hydroxy group; an amino group; a hydrazine group; a sulfonyl group; —SH; an optionally substituted, branched or straight chain aliphatic group having 1 to 8 carbon atoms in a backbone structure that optionally contains nitrogen, oxygen, sulfur, and phosphorus, wherein said aliphatic group optionally has one or more double or triple bonds; an optionally substituted aryl group having 3 to 12 carbon atoms in a backbone structure that optionally contains nitrogen, oxygen, sulfur, and phosphorus; an optionally substituted arylalkyl group having 3 to 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to a linker moiety, wherein when $R_1$, $R_a$, or $R_c$ is an aryl or arylalkyl group having fewer than 5 carbon atoms in a backbone structure, said backbone structure further comprises one or more oxygen and/or nitrogen atoms, wherein W for each monomeric unit is independently selected from an optionally substituted, branched or straight chain divalent moiety having from 1 to about 50 atoms and optionally, one or more double or triple bonds in a backbone that contains carbon and optionally contains nitrogen, oxygen, sulfur, and phosphorus, wherein said optional substitution of W may be a lipid moiety that is optionally bonded to a linker moiety, wherein said lipid moiety is a hydrophobic or amphipathic moiety selected from the group consisting of:

(i) optionally substituted aryl or arylalkyl moieties having from about 14 to about 50 carbon atoms in a backbone structure that optionally contains nitrogen, oxygen, sulfur, and phosphorus, wherein the alkyl group of said arylalkyl optionally has one or more double or triple bonds; and (ii) optionally substituted, branched or straight chain aliphatic moieties having from about 10 to about 50 carbon atoms in a backbone structure that optionally contains nitrogen, oxygen, sulfur, and phosphorus, wherein said aliphatic moieties optionally have one or more double or triple bonds, and wherein at least one of $R_a$, $R_c$, W for a single monomeric unit and $R_1$ for a single monomeric unit comprises a lipid moiety.

Lipid-conjugated polyamides of the present invention can be random polymers where each $R_1$ and W randomly varies from monomer to monomer (i.e., where n is 1 and m is an integer from about 2 to about 48). Alternatively, the lipid-conjugated polyamides can be polymers having m number of n-mers (i.e., where n is greater than 1 and m is an integer from about 2 to about 48) that are either repeating (i.e., each n-mer is the same) or randomly variable (i.e., the monomer composition of each n-mer is random).

Typically, the integer n is not more than about 40, more typically not more than about 20, and even more typically not more than about 6. Preferably, n is about 3. The integer m is typically not more than about 40, more typically not more than about 25. Usually, the integer m is not more than about 15, typically not more than about 12, and even more typically not more than about 8.

When $R_1$, $R_a$, and $R_c$ are aliphatic, they typically contain at least 2 carbon atoms in a backbone structure and more typically contain at least about 3 carbon atoms in a backbone structure. Aryl and arylalkyl $R_1$, $R_a$, and $R_c$ groups can be linear or cyclic. Aryl and arylalkyl $R_1$, $R_a$, and $R_c$ having less than 5 carbon atoms in a backbone structure, also have one or more heteroatoms in the backbone structure, such as, nitrogen and/or oxygen. Typically aryl and arylalkyl $R_1$, $R_a$, and $R_c$ have at least about 5 carbon atoms in a backbone structure.

$R_a$ is typically —OH, —H, —SH, —COOH, sulfonyl, or a lipid moiety optionally conjugated to a linker moiety Rc is typically —OH, —H, —SH, —NH$_2$, sulfonyl, hydrazine, or a lipid moiety optionally conjugated to a linker moiety. Preferably, either $R_a$ or $R_c$ is a lipid moiety optionally conjugated to a linker moiety.

$R_1$ can be a sidechain that is cationic, anionic, or neutral at physiological relevant pH. Typically, physiological pH is at least about 5.5 and typically at least about 6.0. More typically, physiological pH is at least about 6.5. Usually, physiological pH is less than about 8.5 and typically less than about 8.0. More typically, physiological pH is less than about 7.5.

Suitable cationic sidechains include, for example, aminoalkyl (e.g., aminoethyl, aminopropyl, aminobutyl, aminopentyl, and the like) as well as derivatives thereof; (S)-α-methylethylenediamino and derivatives thereof; trimethylaminoethyl and derivatives thereof; guanidinoalkyl (e.g., guanidinoethyl, guanidinopropyl, guanidinobutyl, guanidinopentyl, and the like) and derivatives thereof; aminobenzyl and derivatives thereof; pyridinium and derivatives thereof; and other like cationic moieties that are known to those of ordinary skill in the art.

Suitable neutral sidechains include, for example, (S) or (R)-α-methylbenzyl and derivatives thereof; benzyl and derivatives thereof; phenethyl and derivatives thereof; naphthylmethyl and derivatives thereof; (S) or (R)-α-methylnaphthyl and derivatives thereof; N-propylpyrrolidinone and derivatives thereof; cyclohexylmethyl and derivatives thereof; furfuryl and derivatives thereof; 3,4,5-trimethoxybenzyl and derivatives thereof; methoxyethyl and derivatives thereof; p-methoxyphenethyl and derivatives thereof; isoamyl ("IsoA") and derivatives thereof; and other like neutral moieties that are known to those of ordinary skill in the art.

Suitable anionic sidechains include, for example, carboxy methyl, carboxy ethyl, and the like, and derivatives thereof; benzoic acid and derivatives thereof; phosphates and derivatives thereof; sulfates and derivatives thereof; and other like anionic moieties that are known to those of ordinary skill in the art.

Optionally, $R_1$ can be a moiety found on naturally- or non-naturally-occurring amino acids, or $R_1$ can be a lipid moiety optionally bonded to a linker moiety. As used herein, the term "naturally-occurring amino acid" refers to Ala, Cys, Asp, Glu, Phe, His, Ile, Lys, Leu, Met, Asn, Gln, Arg, Ser, Thr, Val, Trp, and Tyr). The term "non-naturally-occurring amino acid" refers to amino acids typically not found in nature, including, for example, D-isomers of naturally-occurring amino acids.

Typically $R_1$ is not hydrogen for at least two monomeric units, more typically $R_1$ is not hydrogen for at least three monomeric units if n×m is 3 or more. Typically, less than about 75% of the monomer units have an $R_1$ that is hydrogen. More typically, less than about 50% of the monomer units have an $R_1$ that is hydrogen. Even more typically, less than about 25% of the monomer units have an $R_1$ that is hydrogen. Even more typically $R_1$ is not hydrogen for any of the monomeric units.

W is typically $-CH_2CH_2-$, $-CH_2-C_6H_4-C(=O)O-$ (i.e., toluic acid), $-CH_2CH_2-O-$, $-CH_2-CH=CH-$, or $$-CR_2R_3-, \qquad (II)$$

where $R_2$ and $R_3$ for each monomeric unit is independently selected from a hydrogen atom; a hydroxy group; an amino group; a carboxyl group; a sulfonyl group; $-SH$; an optionally substituted, branched or straight chain aliphatic group having 1 to 8 carbon atoms in a backbone structure that optionally contains nitrogen, oxygen, sulfur, phosphorus, and the like, wherein said aliphatic group optionally has one or more double or triple bonds; an optionally substituted aryl group having 3 to 12 carbon atoms in a backbone structure that optionally contains nitrogen, oxygen, sulfur, phosphorus, and the like; an optionally substituted arylalkyl group having 3 to 12 carbon atoms in a backbone structure that optionally contains nitrogen, oxygen, sulfur, phosphorus, and the like, wherein the alkyl group of said arylalkyl optionally has one or more double or triple bonds; and a lipid moiety that is optionally bonded to a linker moiety, wherein when either $R_2$ and $R_3$ is an aryl or arylalkyl group having fewer than 5 carbon atoms in a backbone structure, said backbone structure further comprises one or more oxygen and/or nitrogen atoms.

When $R_2$ and $R_3$ are aliphatic, they typically contain at least 2 carbon atoms in a backbone structure and more typically contain at least about 3 carbon atoms in a backbone structure. Aryl and arylalkyl $R_2$ and $R_3$ groups can be linear or cyclic. Aryl and arylalkyl $R_2$ and $R_3$ having less than 5 carbon atoms in a backbone structure, also have one or more heteroatoms in the backbone structure, such as, nitrogen and/or oxygen. Typically aryl and arylalkyl $R_2$ and $R_3$ have at least about 5 carbon atoms in a backbone structure.

$R_2$ and $R_3$ typically are moieties found on naturally-occurring and non-naturally-occurring amino acids. Usually, at least one of $R_2$ and $R_3$ is a hydrogen atom. Most typically, $R_2$ and $R_3$ are both hydrogen for all monomeric units, such that compound (I) is a lipid-conjugated, N-substituted polyglycine compound.

The lipid moiety can be positioned at $R_a$, $R_c$, $R_1$ for one or more monomers, or at a substitution position in W for one or more monomers. Lipid moieties can be bonded directly to a monomeric unit, or they can be bonded indirectly to a monomeric unit via a linker moiety.

The term "linker" used herein refers to a moiety that functions to couple the oligomeric amide and lipid moieties together in a manner such that the molecular distance between the two moieties is greater than would be if the lipid and oligomeric amide moieties were coupled directly to each other. Linker moieties can be relatively small, having from 1 to about 20 atoms in a backbone, or alternatively polymeric. Small linker moieties are optionally substituted and typically have from 1 to about 20 atoms in a backbone (e.g., carbon, nitrogen, oxygen, sulfur, phosphorus, and the like). Typically, small linker moieties have less than about 18 atoms in a backbone, and more typically, less than about 15 atoms in a backbone. Usually, small linker moieties have less than about 10 atoms in a backbone, and optionally have less than about 5 atoms in a backbone.

Linker moieties can be derived from bifunctional molecules such as, for example, 6-aminohexanoic acid, 2-(2-(2-aminoethoxy)ethoxy)ethoxy)acetic acid, and the like) that are capable of reacting with both oligomeric and lipid reactants. Linker moieties also can be derived from groups such as, for example, acyl and substituted-acyl groups, sulfonyl and substituted-sulfonyl groups, and other like reactive moieties that are employed during chemical synthesis to facilitate conjugation of the lipid moiety to the oligomer moiety.

Polymeric linker moieties are optionally substituted (e.g., hydroxy-, carboxy-, phosphor amino-, and the like), substantially linear polymers having a backbone that contains carbon, and optionally contains nitrogen, oxygen, sulfur, phosphorus, and the like. Polymeric linker moieties have an average molecular weight between about 300 daltons and about 15,000 daltons, typically less than about 10,000 daltons, more typically less than about 5,000 daltons, and even more typically less than about 3000 daltons, and optionally less than about 1000 daltons. Suitable polymeric linker moieties include, for example, polyethylene glycols, polypropylene glycols, polyvinyl alcohols, polyvinylpyrrolidones, and the like.

Lipid moieties are hydrophobic moieties or amphipathic moieties that are either neutral (i.e., having no charge or a net charge of zero) or charged, and either naturally or synthetically derived. Typically, the lipid moiety in lipid-conjugated polyamide compounds of the present invention is amphipathic.

Suitable lipid moieties include: (1) optionally, aryl or arylalkyl moieties having from about 14 to about 50 carbon atoms in a backbone structure that optionally contains nitrogen, oxygen, sulfur, phosphorus, and the like, where the arylalkyl moiety optionally has one or more double or triple bonds; (2) optionally, branched or straight chain aliphatic moieties having from about 10 to about 50 carbon atoms in a backbone structure that optionally contains nitrogen, oxygen, sulfur, phosphorus, and the like, and optionally has one or more double or triple bonds.

Typically, aryl and arylalkyl lipid moieties have at least about 16 carbon atoms and more typically have at least about 20 carbon atoms, and even more typically at least about 30 carbon atoms.

Aliphatic lipid moieties employed in compounds of the present invention typically have at least about 12 carbon atoms and more typically have at least about 14 carbon atoms. Usually, the aliphatic lipid moieties have at least about 18 carbon atoms, more usually at least about 24 carbon atoms, and even more usually at least about 30 carbon atoms.

The number of lipid moieties in lipid-conjugated polyamide compounds of the present invention can vary depending on the degree of hydrophobicity desired, and will also vary with oligomer length (i.e., n×m) and size of lipid moiety. For example, when the lipid moiety has about 30 carbon atoms or less, lipid-conjugated polyamide compounds of the present invention typically have conjugated to it, a number of lipid moieties that is less than the number computed as 90% of the total number of monomeric groups (i.e., n×m) (i.e., if n is 3 and m is 3, then the number of lipid moieties conjugated to the lipid-conjugated polyamide compound is typically less than about 8). More typically, when the lipid moiety has about 30 carbon atoms or less, lipid-conjugated polyamide compounds of the present invention have conjugated to it, a number of lipid moieties that is less than about 80% of the total number of monomeric groups, more typically less than about 75% of the total number of monomeric groups, and even more typically less than about 60% of the total number of monomeric groups.

When the lipid moiety has more than about 30 carbon atoms, typically, lipid-conjugated polyamide compounds of the present invention have conjugated to it a number of lipid moieties that is less than the number computed as 50% of the total number of monomeric groups.

Suitable lipid moieties include those having one or more hydrophobic tails that are optionally substituted aliphatic, straight chain moieties, each independently having from about 8 to about 30 carbon atoms in a backbone that in addition, optionally contains nitrogen, oxygen, sulfur, phosphorus, and the like. Typically, hydrophobic tails have at least about 10 carbon atoms in a backbone and more typically have at least about 12 carbon atoms in a backbone. Hydrophobic tails employed in lipid-conjugated polyamide compounds of the present invention typically do not have more than about 26 carbon atoms in a backbone, and more typically do not have more than about 24 carbon atoms in a backbone.

Natural lipid moieties employed in the practice of the present invention can be derived from, for example, phospholipids, including, for example, phosphoglycerides (including both acyl phosphoglycerides (such as, for example, phosphatidic acid, phosphatidyl ethanolamine, phosphatidyl serine, phosphatidyl inositol, phosphatidyl inositol phosphate, phosphatidyl inositol bisphosphate, phosphatidyl glycerol, diphosphatidylglycerol, and the like) and ether phosphoglycerides); glycosylglycerides (such as, for example, monogalactosyl diacylglycerol, digalactosyldiacylglycerol, sulphoquinovosyldiacylglycerol, dimannosyldiacylglycerol, galactofuranosyldiacylglycerol, galactosylglucosyldiacylglycerol, galactosylglucosyldiacylglycerol, glucosylgalactosylglucosyldiacylglycerol, and the like); sphingolipids (such as, for example, sphingosines, glycosyl ceramides, gangliosides, and the like); and saturated and unsaturated sterols (such as, for example, cholesterol, ergosterol, stigmasterol, sitosterol, and the like); and other like natural lipids.

Suitable synthetic lipid moieties can be derived from, for example, dipalmitoyl phosphatidylethanolamine (DMPE) (Genzyme Corp., Cambridge), DMRIE-C™ (GibcoBRL, Gaithersburg, Md.), 2,3-dioleyloxy-N-[2(spermine-carboxamido)ethyl]-N,N-dimethyl-1-propanaminiumtrifluoroacetate (DOSPA) (Lipofectamine™, GibcoBRL, Gaithersburg, Md.), 3β-[N—(N',N'-dimethylaminoethyl)carbamoyl]cholesterol, Tfx-50 (Promega Corp., Madison, Wis.), N,N1,N2,N3-tetramethyl-N,N1,N2,N3-tetrapalmitylsperimine (TM-TPS) (Cellfectin, GibcoBRL, Gaithersburg, Md.), dipalmitoyl phosphatidylethanolaminospermine, and the like.

Suitable lipid moieties also include those derived from fatty acids and fatty alcohols having from about 8 to about 24 carbon atoms in a backbone. Typically, the fatty acids and fatty alcohols have at least about 10 carbon atoms in a backbone, and more typically have at least about 12 carbon atoms in a backbone. Usually, the fatty acids and alcohols from which lipid moieties are derived have less than about 20 carbon atoms in a backbone.

Typically, $R_a$ is a lipid moiety or a lipid moiety conjugated to a linker moiety. A particularly useful lipid moiety-containing $R_a$ group is the phosphatidyl alkylamino-substituted acyl moiety having the formula, $$R_4\text{—CO—O—}CH_2CH(O\text{—CO—}R_4)\text{—}CH_2\text{—O—}PO_3^-\text{—}(CH_2)_p\text{—}NH_2^+\text{—}CH_2\text{—CO—}, \quad \text{(III)}$$

where p is an integer selected from 2 or 3, and each $R_4$ is independently selected from an alkyl or alkenyl moiety having between about 6 and about 25 carbon atoms in a backbone. Typically $R_4$ has up to about 22 carbon atoms in a backbone, more typically, up to about 20 carbon atoms, even more typically up to about 18 atoms. Typically, $R_4$ has at least about 8 carbon atoms in a backbone, more typically at least about 10 carbon atoms, and even more typically at least about 12 carbon atoms in a backbone. Exemplary $R_4$ moieties include dodecyl, tridecyl, tetradecyl, pentadecyl, hexadecyl, heptadecyl, octadecyl, and the like. Preferably p is 2.

Lipid-conjugated polyamide compounds of the present invention can be optionally further conjugated or complexed with agents that impart, for example, targeting capabilities, structural features, biological activity, or that introduce degradations sites, and the like. Suitable agents include, for example, mono-, di-, and polysaccharides, polyethylene glycols, amino acids, peptides, polypeptides, proteins (including, for example, lipoproteins, glycoproteins, antibodies, and the like), crosslinking agents, marker agents (such as, for example, fluoroscein, biotin, $^{32}P$, and the like), and the like.

Those of ordinary skill in the art will appreciate that $R_1$, $R_c$, $R_a$, W, and the particular lipid moiety employed can be readily varied to optimize the physicochemical properties of the lipid-conjugated polyamide compound for delivery of a particular type of polynucleotide. For example, oligomeric moieties of the present invention suitable for use in the delivery of siRNA to cells have a net positive charge and are capable of condensing polynucleic acids so that they are more compact in size, thus facilitating their delivery to cells.

Compounds of formula (I) that are suitable for use in the delivery of siRNA to cells, include lipid-conjugated polyamide compounds having repeating n-mer units (i.e., where n is greater than 1). For example, when n is 3, the lipid-conjugated polyamide compound of formula (I) has repeating trimer units, i.e.,

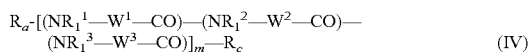

$$R_a-[(NR_1^1-W^1-CO)-(NR_1^2-W^2-CO)-(NR_1^3-W^3-CO)]_m-R_c \quad (IV)$$

where $R_a$, $R_c$, m, each W and each $R_1$ are defined as in formula (I), and positional isomers thereof. Compounds having formula (IV) that are suitable for use in the delivery of siRNA to cells include those where $R_1^1$ is a cationic side chain, $R_1^2$ and $R_1^3$ are both neutral side chains, each W is $CH_2$, $R_c$ is $NH_2$, and $R_a$ is defined by formula (III).

Lipid-conjugated polyamide compounds of the present invention typically form concentration-dependent, ordered two- or three-dimensional structures in solution. Such structures include two dimensional arrays, such as, for example, a single charged layer or a lipid bilayer surface, and three-dimensional structures, such as, for example, micelles, vesicles, and liposomes. Typically, ordered structures formed from lipid-conjugated polyamide compounds of the present invention by themselves, typically are sufficiently small such that they do not scatter light. Micelles, vesicles, and liposomes prepared from lipid-conjugated compounds complexed with polynucleotides typically have average particle sizes that are less than about 1 μm, more typically less than about 500 nm, and even more typically less than about 200 nm.

In particular embodiments, a lipid-conjugated polyamide compound-based delivery vehicle of the present invention may include one or more lipid-cationic peptoid conjugates of the formula:

$$L-X-[N(CH_2CH_2NH_2)CH_2(C=O)-N(CH_2CH_2R)\\CH_2(C=O)-N(CH_2CH_2R)CH_2(C=O)]_3-NH_2 \quad (VI)$$

and positional isomers
where
L is selected from a non-steroidal lipid moiety comprising at least one fatty alkyl or alkenyl chain between about 8 and 24 carbon atoms in length, and a sterol moiety;
each group R is independently selected from alkyl, aminoalkyl, and aralkyl, and
X is selected from the group consisting of a direct bond, an oligopeptide, a substantially linear alkyl chain from 2 to about 30 bonds in length, and a substantially linear chain from 2 to about 30 bonds in length consisting of alkyl bonds and one or more linkages selected from the group consisting of ester, amide, carbonate, carbamate, disulfide, peptide, and ether.

When L is a non-sterol lipid moiety (that is, a lipid moiety that does not contain a sterol group, such as a phospholipid group (i.e., $ROOCCH_2CH(COOR)CH_2OP(O)_2O-$), the lipid-cationic polyamide conjugate is referred to herein as a "lipitoid." When L is a sterol moiety, (that is, a lipid moiety that does contain a sterol group, such as a cholesterol group), the lipid-cationic polyamide conjugate is referred to herein as a "cholesteroid." The lipid-cationic polyamide conjugate in a composition of the present invention may be a lipitoid, a cholesteroid, or, in one important embodiment, a combination thereof.

In specific embodiments, R is isopropyl or 4-methoxyphenyl. A single lipitoid or cholesteroid may include different groups R, or they may be the same within the molecule.

These vehicles may be prepared by conventional solution or solid-phase synthesis, such as are described in Zuckermann et al. cited above, and further detailed below. In one such procedure, the N-terminus of a resin-bound peptoid is acylated with a spacer such as Fmoc-aminohexanoic acid or Fmoc-β-alanine. After removal of the Fmoc group, the primary amino group is reacted with a lipid moiety, such as cholesterol chloroformate, to form a carbamate linkage, e.g. as shown in Cholesteroids 1 and 3 of FIG. 1. The product is then cleaved from the resin with trifluoroacetic acid and purified by reverse-phase HPLC. A fatty acid-derived lipid moiety, such as a phospholipid, may be used in place of the steroid moiety, to form lipitoids as described herein and also shown in FIG. 1.

The lipid moiety may also be linked to the polyamide, e.g., peptoid, moiety by other linkages, of any effective length, readily available to the skilled practitioner. The linker is a chain up to about 30 bonds in length, and more preferably up to about 15 bonds in length, though any effective length may be used. The chain is typically linear or substantially linear, although branched chains (including oligopeptides) and linkers containing intervening cyclic groups can also be used. The linker generally comprises alkyl (C—C) bonds and one or more functional groups such as ester, amide, carbonate, carbamate, disulfide, peptide or ether bonds. The linker may comprise multiple functional groups, as in a succinate ester or polyether, or it may be an oligopeptide, preferably a 2- to 10-mer, and more preferably a 2- to 5-mer. The steroid or lipid moiety and peptoid segment can also be joined by a direct bond.

In certain embodiments, the linker incorporates one or more bonds which are susceptible to cleavage under appropriate conditions in vivo; for example, hydrolyzable ester, carbonate, carbamate, or peptide bonds; disulfide bonds, which are cleavable in cellular compartments having a sufficiently reducing environment; and peptide bonds, cleavable by endogenous peptidases. With respect to the latter, polypeptide linkers having ten or fewer, or, in further embodiments, five or fewer peptide linkages are contemplated, though longer linkers may also be used.

Representative structures of this class, shown in FIG. 1 are given the following designations herein:

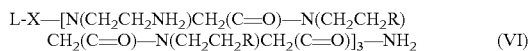

| | |
|---|---|
| Lipitoid 1, or L1 | DMPE(NaeNmpeNmpe)$_3$ |
| Lipitoid 2, or L2 | DMPE(NaeNiaNia)$_3$ |
| Lipitoid 3, or L3 | NtdNhd(NaeNmpeNmpe)$_3$ |
| Lipitoid 4, or L4 | NddNol(NaeNmpeNmpe)$_3$ |
| Cholesteroid 1, or C1 | Chol-β-ala-(NaeNmpeNmpe)$_3$ |
| Cholesteroid 3, or C3 | Chol-β-ala-(NaeNiaNia)$_3$ | wherein "Ntd" is N-tetradecylglycine; "Nhd" is N-hexadecylglycine; "Ndd" is N-dodecylglycine; "Nol" is N-oleylglycine.

The peptoid monomers represented in the foregoing structures are as follows:

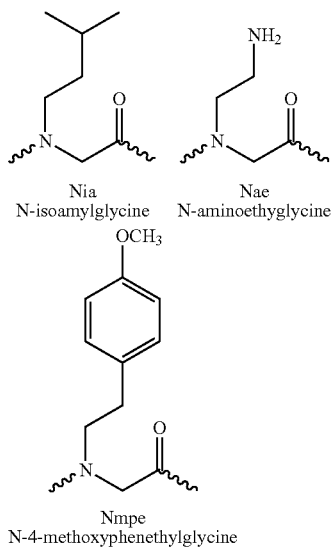

Nia
N-isoamylglycine

Nae
N-aminoethyglycine

Nmpe
N-4-methoxyphenethylglycine

In one aspect, the invention provides a biological agent delivery vehicle composed of a mixture of at least one lipitoid and one cholesteroid. The delivery vehicle is suitable for delivery of a variety of polynucleotides, such as plasmid DNA, antisense oligonucleotides and siRNA, to cells, where the delivery vehicle is combined with the polynucleotide(s) in a composition in accordance with the present invention.

Compositions in accordance with the invention result in efficient delivery of the siRNA to mammalian cells effective knockout of target gene mRNA. Compositions and delivery vehicles in accordance with the present invention may be used in vitro, for example in connection with research including drug discovery, development and testing activities, or in vivo for therapeutic applications (e.g., as drugs of drug components for treating disease) in animal, including mammalian (e.g., human) subjects. For such in vivo applications, a pharmaceutically acceptable vehicle in accordance with the present invention is used.

Synthesis of Lipid-Conjugated Polyamide Compounds

Lipid-conjugated polyamide compounds suitable for use in compositions of the present invention can be synthesized by solid-phase and solution-phase methods. The present invention also provides a method of synthesizing lipid-conjugated polyamide compounds, said method comprising:

a) contacting
(1) a lipid reactant, with
(2) an oligomer reactant, wherein said oligomer reactant has the general formula:

$$T_a[(NR_1\text{---}W\text{---}CO)_n]_m\text{-}T_c \qquad (V)$$

wherein n is an integer selected from 1 to about 48, and m is an integer from about 2 to about 48, wherein each $T_a$ and $T_c$ is independently selected from a terminal group and a reactive moiety that is capable of further reaction with said lipid reactant, wherein $R_1$ for each monomeric unit, —(NR$_1$—W—CO)—, in said oligomer reactant is selected from the group consisting of a hydrogen atom; a hydroxy group; an amino group; a carboxyl group; a sulfonyl group, —SH; an optionally substituted, branched or straight chain aliphatic group having 1 to 8 carbon atoms in a backbone structure that optionally contains nitrogen, oxygen, sulfur, and phosphorus, wherein the aliphatic group optionally has one or more double or triple bonds; an optionally substituted aryl group having 3 to 12 carbon atoms in a backbone structure that optionally contains nitrogen, oxygen, sulfur, and phosphorus; an optionally substituted arylalkyl group having 3 to 12 carbon atoms in a backbone structure that optionally contains nitrogen, oxygen, sulfur, and phosphorus, wherein the alkyl group of said arylalkyl optionally has one or more double or triple bonds; and a reactive moiety that is capable of further reaction with said lipid reactant, wherein when $R_1$, $R_a$, or $R_c$ is an aryl or arylalkyl group having fewer than 5 carbon atoms in a backbone structure, said backbone structure further comprises one or more oxygen and/or nitrogen atoms, wherein $R_1$ is not a hydrogen atom for at least one monomeric unit, wherein W for each monomeric unit is selected from an optionally substituted, branched or straight chain divalent moiety having from 1 to about 50 atoms in a backbone that contains carbon, and optionally contains nitrogen, oxygen, sulfur, and phosphorus, and optionally one or more double or triple bonds, wherein said optional substitution of W may be a reactive moiety that is capable of further reaction with said lipid reactant, wherein at least one of $T_a$, $T_c$, W for a single monomeric unit, or $R_1$ for a single monomeric unit comprises a reactive moiety that is capable of further reaction with said lipid reactant; then b) reacting said lipid reactant with said oligomer reactant to conjugate the lipid reactant to the oligomer reactant.

The term "lipid reactant" used herein refers to a reactive species having a lipid moiety that is capable of participating in a chemical reaction, such as, for example, nucleophilic displacement, condensation, and the like. Lipid reactants having functional groups, such as, for example, —NH$_2$, —COOH, —SH, —OH, —SO$_2$Cl, and —CHO are particularly useful for synthesizing lipid-conjugated compounds of the present invention. Lipid reactants suitable for use in the practice of the present invention include lipid reactants having any one of the lipid moieties described herein which can react with, or which can be modified to react with, the oligomeric reactant or a linker. Typically, lipid reactants are primary, secondary, or tertiary amines. Specific lipid reactants suitable for use herein are phosphatidylethanolamines.

As used herein, the term "oligomer reactant" refers to an oligomeric amide that is capable of participating in a chemical reaction, such as, for example, nucleophilic displacement, condensation, and the like. Oligomer reactants typically are acylated with a leaving group that is susceptible to nucleophilic displacement by a nucleophile, such as an amine. Oligomer reactants suitable for use in the practice of the present invention include all of the oligomeric amide substituents described for formula (I) (i.e.—[(NR$_1$—W—CO)$_n$]$_m$—) herein.

As used herein, the term "reactive moiety" refers to a moiety that is capable of participating in a reaction with the lipid reactant. Typical reactive moieties include, for example, —NH$_2$, —OH, —H, —SH, —COOH, acyl (e.g., acetyl), benzoyl, sulfonyl (e.g., dansyl), amide, hydrazine (typically a $T_c$ group), and derivatives thereof (including alkyl-substituted derivatives), and the like. Typically, the reactive moiety is an acyl moiety substituted with a leaving group that is susceptible to nucleophilic displacement by a nucleophile, such as an amine.

Exemplary terminal groups include moieties that are biologically active agents, targeting agents (e.g., a cell receptor ligand, antibody, etc.), marker agents, amino acid residues that function, for example, as a degradation site for endogenous proteolytic enzymes, and the like. These terminal groups typically are not further reactive with the lipid reactant.

The oligomer reactant and lipid reactant can be optionally bonded to each other via a linker moiety (which optionally can be derived from a reactive moiety). Alternatively, the linker moiety, which is derived from a molecule that is capable of reacting with both oligomeric and lipid reactants, can be optionally conjugated to either the lipid or oligomer reactant prior to reaction between lipid and oligomer reactants. Thus, the lipid reactant can be conjugated to the oligomer reactant either directly, or indirectly via the linker moiety.

The term "reacting" used herein refers to one or more chemical reactions that result in formation of a chemical bond between the lipid reactant and the oligomer reactant, either directly, or indirectly via the linker moiety. Suitable reactions include, for example, condensation (e.g., acylation, and the like) and nucleophilic displacement.

Oligomer reactants having the general formula (IV) can be prepared, for example, via a series of nucleophilic displacement reactions according to the solid-phase method described by Zuckermann et al., PCT WO94/06451 (published Mar. 31, 1994), incorporated herein by reference. The method can be performed utilizing automated peptide synthesis instrumentation to permit rapid synthesis of oligomer reactants of interest. These instruments are commercially available from, for example, Applied Biosystems.

Specifically, monomer assembly into oligomer reactants is achieved by the sequential addition of "submonomer" units to the growing chain. In one method of monomer assembly, each cycle of monomer addition consists of two steps:

(1) acylation of a secondary amine bound to the solid support with an acylating agent that has a leaving group (i.e., a group susceptible to nucleophilic displacement by a nucleophile, such as an amine) and a carbonyl group (e.g., a carboxyl group) (i.e., the "acylation step"); followed by (2) nucleophilic displacement of the leaving group with a sufficient amount of a submonomer that has a primary, secondary, or tertiary amino group to introduce a side-chain (i.e., the "nucleophilic displacement step").

Exemplary acylating agents include haloacetic acid, halomethyl benzoic acid, and the like. The efficiency of displacement of the leaving group is modulated by the type of acylating agent employed. For example, when a haloacetic acid is employed, it has been observed that iodine is more efficient at displacing the leaving group compared to chlorine. Suitable submonomers include alkylamines, alkenylamines, aromatic amines, alkoxyamines, semicarbazides, acyl hydrozides, and derivatives thereof, and the like.

Oligomer synthesis using the submonomer approach occurs in the carboxy to amino direction. The oligomer is elaborated until the desired length, then is terminated, for example, with a bromoacetamide group. One advantage of using solid phase submonomer assembly to construct oligomer reactants of the present invention is that the need for N-α-protected monomers is eliminated, as only reactive side-chain functionalities need to be protected.

Typically, the oligomeric reactant is synthesized as a series of repeating di-, tri-, or tetra-mer units. An exemplary trimer-based cationic oligomer has the following monomer sequence in the amino terminal ($T_a$) to carboxy terminus ($T_c$) direction:

(1) positively charge monomer
(2) neutral monomer, and
(3) neutral monomer.

The terms "neutral monomer" and "positively charged monomer" as used herein refer to the net charge of the monomeric unit. As noted above, in other examples in accordance with the present invention, other positional isomer motifs may be used, for example neutral-positive-neutral; or neutral-neutral-positive.

Further reaction of the oligomer reactant with the lipid reactant can occur by further acylation and/or nucleophilic displacement. For example, an oligomer reactant that is haloacylated (e.g., where $T_a$ is a bromoacetyl group) can be reacted with an lipid reactant that is a primary, secondary, or tertiary amine. Conjugation thus occurs by nucleophilic displacement of the bromine, to form a lipid-conjugated polyamide compound.

More specific details are provided in the following solid-phase submonomer synthesis protocol for lipid-cationic peptoid conjugates, including lipitoids and cholesteroids, in accordance with specific embodiments of the present invention:

General Experimental

Reagent grade solvents are used without further purification. Bromoacetic acid may be obtained from Aldrich (99% grade) and DIC may be obtained from Cheminplex International. All reactions and washings are performed at 35° C. unless otherwise noted. Washing of the resin refers to the addition of a wash solvent (usually DMF or DMSO) to the resin, agitating the resin so that a uniform slurry is obtained (typically for about 20 seconds), followed by thorough draining of the solvent from the resin. Solvents are best removed by vacuum filtration through the fritted bottom of the reaction vessel until the resin appears dry (typically about 10 seconds). Resin slurries are agitated via bubbling argon up through the bottom of the fritted vessel. Solvents used to dissolve reagents should be degassed prior to use by sonication under house vacuum for 5 minutes. For wash solvents, it is very convenient to have dispensers containing DMF, DMSO and dichloromethane available with adjustable volumes (1-5 mL).

If synthesis is halted and the resin is to be stored for a length of time (overnight), it is recommended that the resin be rinsed well with methylene chloride before storage. Resins that are to be stored may be further dried under high vacuum. It is advisable to not stop a synthesis at the dimer stage because dimers can cyclize upon storage over a long period of time to form diketopiperazines.

Initial Resin Swelling and Fmoc Deprotection.

A fritted reaction vessel is charged with 100 mg of Fmoc-Rink amide resin (0.50 mmol/g resin). To the resin is added 2 mL of DMF and this solution is agitated for 5 minutes to swell the resin. A glass rod may be used to break up chunks of resin, if necessary. The DMF is then drained. The Fmoc group is then removed by adding 2 mL of 20% piperidine in DMF to the resin. This is agitated for 1 minute, then drained. Another 2 mL of 20% piperidine in DMF is added to the resin and agitated for 20 minutes, then drained. The resin is then washed with DMF (5×2 mL).

Submonomer Synthesis Cycle.

The deblocked amine is acylated by adding to the resin 850 μL of 1.2 M bromoacetic acid in DMF, followed by 175 μL neat N,N'-diisopropylcarbodiimide (DIC). This solution is agitated for 20 minutes at 35° C., then drained. The resin is then washed with DMF (3×2 mL) and DMSO (1×2 mL).

The acylation step (step 1) is then followed by nucleophilic displacement with a primary amine (step 2). To the washed resin is added 0.85 mL of a 2 M solution of the amine in DMSO. This solution is agitated for 30 min at 35° C. and then drained. The resin is then washed with DMSO 3×2 mL) and DMF (1×2 mL). This completes one reaction cycle.

The acylation/displacement cycle is repeated until the desired oligomer is obtained. The submonomer synthesis reaction scheme is illustrated below:

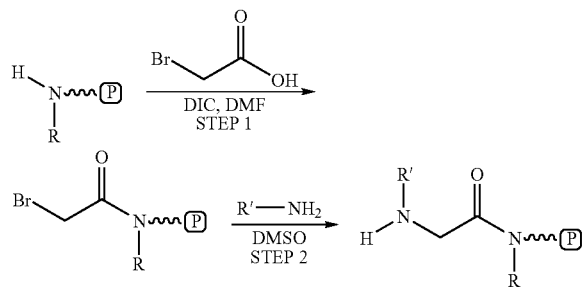

Cleavage (for 50 μmol Resin).

After the synthesis reaction and resin washing, the resin is washed with dichloromethane (2×2 mL) and dried in vacuo for two hours. Prepare a solution of trifluoroacetic acid (95%, aqueous). The dried resin is placed in a glass scintillation vial containing a Teflon micro stir bar, and approximately 5 mL of 95% aqueous TFA is added. The scintillation vials are placed onto a stirring plate located in a fume hood. One stirring plate can accommodate four or five vials at a time. This solution is stirred for 20 minutes. The cleavage mixture is filtered for each sample through an 8 mL solid phase extraction (SPE) column fitted with a 20 μm polyethylene frit into a 50 mL polypropylene conical centrifuge tube. The cleavage time may need to be lengthened depending upon which protecting groups are present in a particular library. The resin is then washed with 1 mL of the 95% TFA and the filtrates are combined. The filtrate is then diluted with an equal volume of water in the centrifuge tube.

This solution is then frozen and lyophilized to dryness. By puncturing small holes in the caps of the vials, direct lyophilization from the polypropylene tubes may be conducted. The dried product is then taken up in 10 mL of glacial acetic acid and again lyophilized to dryness. The twice-dried product is then taken up in 3 mL of 1:1 acetonitrile/water and transferred to a tared 5 mL cryovial (preferably with a silicone o-ring) and then lyophilized to dryness, generally producing a white fluffy powder. The mass recovery can then be calculated and the product can remain in the cryovial for cold storage. For the purpose of calculating yields, it may be assumed that the product is the trifluoroacetate salt. Prior to the last lyophilization, HPLC and mass-spec samples should be prepared.

If the material is going to be used for testing in a biological assay, then DMSO is added to make a concentrated stock solution. Solutions at a concentration of 100 μM/per compound or greater are preferred. This 100×DMSO stock may be diluted 1:100 into buffer, yielding an assay solution that contains 1% DMSO, and sample molecules at a concentration of 1 μM per compound (a typical screening concentration). DMSO is a good choice for this because it dissolves peptoids very well, and when diluted is compatible with most biological assays (at concentrations ≤1%).

Oligomer Characterization.

Individual peptoid oligomers are analyzed by reverse-phase HPLC on C-18 columns (Vydac, 5 μm, 300 Å, 4.5×250 mm). A linear gradient of 0-80% B in 40 min is used at a flow rate of 1 mL/min (solvent A=0.1% TFA in water, solvent B=0.1% TFA in acetonitrile). Major peaks are collected and submitted to electrospray MS analysis to determine the molecular weights.

Lipitoid Synthesis (50 μmol Scale).

Lipitoids 1 and 2 (L1 and L2) are standard peptoids where the final (N-terminal) residue is a phosphatidylethanolamine, a primary amine. L1 and L2 use dimyristrylphosphatidylethanolamine (DMPE) as the N-terminal lipid moiety. In order to install this group, the N-terminus is bromacetylated and washed using standard submonomer conditions (above). The resin is then washed with 15% methanol/chlorobenzene (2×2 mL).

A 0.2 M solution of DMPE is then prepared as follows. DMPE (Genzyme) is dissolved in 15% methanol/chlorobenzene to a concentration of 0.2 M. Since this compound is in the zwitterionic form, the compound must be neutralized to obtain the amine free base. This is accomplished by the addition of 0.92 equivalent of 50% aqueous KOH with rapid vortexing. The base addition may leave a small volume of water behind as a separate phase, so the sample should be centrifuged (tabletop centrifuge, max rpm for 1 minute) and any aqueous phase removed. At this stage, the purity of the DMPE solution should be checked by TLC (TLC solvent: 80/20/0.5 $CH_2Cl_2/CH_3OH/NH_4OH$, stain with ninhydrin). The product should have an $R_f$ of ~0.6.

The DMPE (2 mL) solution is then added to the resin. Due to the potential frothiness of this solution, the reaction is mixed very gently (usually by intermittent argon bubbling or rotary shaking). The reaction is incubated at 35° C. overnight. The reaction mixture is then drained and washed with 15% methanol/chlorobenzene (6×3 mL), DCE (2×3 mL) and DCM (1×3 mL). Cleavage is carried out under standard peptoid conditions (see above). Due to the increased lipophilicity of the lipitoids, HPLC analysis should be done on a C4 column.

Lipitoids 3 and 4 (L3 and L4) are standard peptoids where the last 2 N-terminal residues are made with hydrophobic amines. These amines are dissolved in 15% methanol/chlorobenzene at a concentration of 1 M. The displacement reactions are performed with 1 mL of the solution at 50° C. for two hours, followed by washing with 15% methanol/chlorobenzene (3×2 mL) and DMF (3×2 mL).

Cholesteroid Synthesis (50 μmol Scale).

The cholesterol moiety is added by a two-step procedure where a beta-alanine linker is first added to the N-terminus of the desired peptoid ((NaeNmpeNmpe)$_3$ for C1 and (NaeNiaNia)$_3$ for C3) followed by a coupling with cholesterol chloroformate. Fmoc-β-alanine (NovaBiochem) is coupled to the N-terminus by the addition of 2.0 mL of a solution of Fmoc-β-alanine (0.4 M) and HOBt (0.4 M) in DMF, followed by the addition of 1.1 equivalents of neat DIC. The reaction mixture is agitated for 1 hour, after which the reaction mixture is drained and the resin is washed with DMF (2×3 mL). The β-alanine coupling is then repeated, after which the resin is washed with DMF (3×3 mL) and DCE (1×3 mL). After Fmoc removal, as described above, the cholesterol moiety is then added by adding 2.0 mL of a 0.4 M solution of cholesterol chloroformate (Aldrich) in DCE, followed by the addition of 1 equivalent of neat diisopropylethylamine (DIEA). The reaction mixture is mixed gently overnight at 35° C. The resin is then washed with DCE (5×3 mL) and DCM (2×3 mL).

Since the carbamate formed is slightly acid-labile, care should be taken in the cleavage and handling of the compound. Cleavage is performed by the addition of TFA/DCE 1:1 (5 mL) for 10 min. The filtrate is collected and the resin washed with an additional 2 mL of cleavage cocktail. The combined filtrates are then dried rapidly in vacuo, and the oil resuspended in 1:1 acetonitrile/water. This is immediately frozen (−80° C.) and lyophilized. The sample should then be lyophilized once more from acetonitrile/water (1:1).

Lipitoid and Cholesteroid Purification.

The lipitoids and cholesteroids are purified by reverse-phase HPLC prior to use. C4 columns may be used. In one example, the compounds are dissolved in a small amount of 25% acetonitrile/water and purified on a 50×20 mm ID Dura-Gel HS C4 column (Peeke Scientific)). A linear gradient of 35-85% B in 40 min is used at a flow rate of 30 mL/min (solvent A=0.1% TFA in water, solvent B=0.1% TFA in acetonitrile). The combined product fractions are combined and lyophilized to a white powder.

Method for Making Lipid-Conjugated Polyamide Compositions

To prepare transfecting compositions, an aqueous solution of a lipid-conjugated polyamide compound vehicle, such as a lipitoid or cholesteroid or mixture, is formulated with the siRNA, as described in Example 1. The components are preferably used in relative amounts such that there are at least 1.5 and preferably two to four, positive vehicle charges for every siRNA negative charge. The exact ratio of siRNA to vehicle is preferably determined empirically for each cell type, but is generally in the range of 1.5-2 nmol vehicle/μg antisense oligonucleotide. Cells may be transfected with compositions in accordance with the present invention as described in Example 1. Further details relating to the use of compositions in accordance with the present invention is provided below.

Use of Lipid-Conjugated Polyamide Compositions

In another aspect, a method of inhibiting expression of a target gene in a cell, which involves administering to the cell a composition as described above, in which one strand of the siRNA duplex has a nucleotide sequence comprised in a mRNA derived from the target gene is provided. The cell may be comprised in a "subject," as defined herein.

The compositions of the present invention comprising lipid-conjugated polyamide compound(s) are capable of delivering an effective amount of a polynucleotide (e.g., siRNA) to cells. As used herein, the term "effective amount" refers to an amount of polynucleotide that is sufficient to detectably induce, or participate in, a biological response, such as, for example, signal transduction, transcription, translation, lymphocyte activation, including, for example, antibody production, and the like.

The relative quantities of lipid-conjugated polyamide compound to polynucleic acid (e.g., siRNA) are typically selected such that the +/− charge ratio of lipid-conjugated polyamide compound to polynucleotide in the composition is at least about 1.5 and less than about 10. More typically, the +/− charge ratio is less than about 8, and even more typically is less than about 4. The charge ratio is computed according to the following:

$$\text{Charge Ratio} = (n_L \times M_L)/(3.03 \times M_{siRNA}),$$

where $n_L$ is the number of moles of lipid-conjugated polyamide compound, $M_L$=net number of charges/mole lipid-conjugated polyamide, and where $M_{siRNA}$=micrograms of siRNA.

Compositions of the present invention can be in liquid or solid form, and can optionally include pharmaceutically acceptable excipients. Such excipients can be used as fillers, processing aids, delivery enhancers and modifiers, and the like. Suitable excipients include, for example, calcium phosphate, magnesium stearate, talc, monosaccharides, disaccharides, polysaccharides, gelatin, cellulose, methyl cellulose, sodium carboxymethyl cellulose, dextrose, polyvinyl alcohol, polyvinylpyrrolidinone, low melting waxes, ion exchange resins, and the like, as well as combinations of any two or more thereof. A thorough discussion of pharmaceutically acceptable excipients is available in "Remington's Pharmaceutical Sciences" (Mack Pub. Co., NJ 1991).

Additional agents can be included in the compositions, such as, for example, marker agents, nutrients, and the like. For example, when the biologically active agent is a polynucleotide, agents that promote endocytosis of the desired nucleic acids or aid in binding of the nucleic acids to the cell surface, or both, can be incorporated into compositions of the present invention.

Liquid compositions of the present invention can be in the form of a solution, suspension, or emulsion with a liquid carrier. Suitable liquid carriers include, for example, water, saline, pharmaceutically acceptable organic solvent(s), pharmaceutically acceptable oils or fats, mixtures thereof, and the like. The liquid carrier may contain other suitable pharmaceutically acceptable additives, such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like.

Cells suitable for use in the practice of the present invention include, for example, mammalian cell lines available from the American Type Culture Collection (ATCC), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, baby hamster kidney cells, mouse sertoli cells, canine kidney cells, buffalo rat liver cells, human lung cells, human liver cells, mouse mammary tumor cells, other mammalian (including human) cells (e.g., stem cells, particularly hemapoitic cells, lymphocytes, macrophages, dendritic cells, tumor cells and the like), and the like.

Suitable tissue for use as samples in the present invention include, for example, tissue derived from mammals, such as, muscle, skin, brain, lung, liver, spleen, blood, bone marrow, thymus, heart, lymph, bone, cartilage, pancreas, kidney, gall bladder, stomach, intestine, testis, ovary, uterus, rectum, nervous system, eye, gland, connective, and the like.

Modes of administration to a sample include, for example, ex vivo administration to samples derived from a subject and in vitro administration to a sample. Methods for carrying out these modes of administration are well known to those of ordinary skill in the art. For example, ex vivo delivery and reimplantation of transformed cells into a subject can be achieved as described in e.g., International Publication No. WO 93/14778 (published Aug. 5, 1993).

As used herein, the term "subject" refers to cells, cell lines (including mammalian cells and cell lines), invertebrates, and vertebrates including birds and mammals, such as, for example, rodents and humans. Direct administration to a subject can typically be accomplished by injection, either subcutaneously, intraperitoneally, intravenously or intramuscularly or delivered to the interstitial space of a tissue. The compositions can also be administered into a tumor or lesion. Other modes of administration include oral and pulmonary administration, suppositories, and transdermal applications, needles, and gene guns or hyposprays.

In addition to the delivery of siRNA (or other polynucleotides) to cells, lipid-conjugated polyamide compounds of the present invention can also be used in applications, such as, for example, screening peptide-like compounds for biological activity, incorporation into biosensors such that the oligomeric moiety has the capacity to bind to a target ligand, and the like. For drug screening applications, for example, libraries of lipid-conjugated polyamide compounds having a variety of $R_1$ groups can be synthesized and subsequently screened for biological activity in accordance with the methods for synthesizing and screening modified peptide libraries described in PCT publication WO 91/19735 (published Dec. 26, 1991), incorporated herein by reference.

EXAMPLES

The following examples illustrate but are not intended in any way to limit the invention.

Example 1

SiRNA Inhibition of Target mRNA

A. Preparation of Transfection Mixture

For each transfection mixture (which are examples of compositions in accordance with the present invention), a lipitoid or lipitoid/cholesteroid combination delivery vehicle was prepared to a working concentration of 0.5 mM in water and mixed to yield a uniform solution. The siRNA was prepared to a working concentration of 20 µM in buffer supplied with the siRNAs. In this example, the siRNAs were for Akt1 mRNA and had the sequence CAUAGUGAGGUUGCAUCUGGUG (SEQ ID No: 1) with two 2' O-methyl UU (RNA) nucleotide 3'-overhangs and phosphodiester links throughout (available from Integrated DNA Technologies). The siRNA was diluted in OptiMEM™ (Gibco/BRL), in a microfuge tube, to 1 µM, or approximately 15 µg oligo/ml of OptiMEM™. In a separate microfuge tube, vehicle, typically in the amount of about 3.75 nmol vehicle/100 pmol siRNA, was diluted into the same volume of OptiMEM™ used to dilute the siRNA. In this example, the starting concentrations of siRNA and vehicle used, this results in about 1.5 µl of vehicle per µl of siRNA used. Note that the exact ratio of siRNA to vehicle must be determined empirically for each cell type, but generally is about this amount. The diluted siRNA was immediately added to the diluted vehicle and mixed by pipetting up and down. The mixture was allowed to incubate at room temperature for 10 minutes.

B. Transfection

Cells were plated on tissue culture dishes one day in advance of transfection, in growth media with serum, to yield a density at transfection of 60-90%. The siRNA/vehicle mixture was added to the cells immediately after mixing and incubation, to a final concentration of 50-100 nM siRNA in half the normal growth medium volume. Cells were incubated with the transfection mixture at 37° C., 5% $CO_2$ for 4-24 hours. After incubation, the transfection mixture was diluted 2 fold with normal growth medium with serum.

Figure 2:
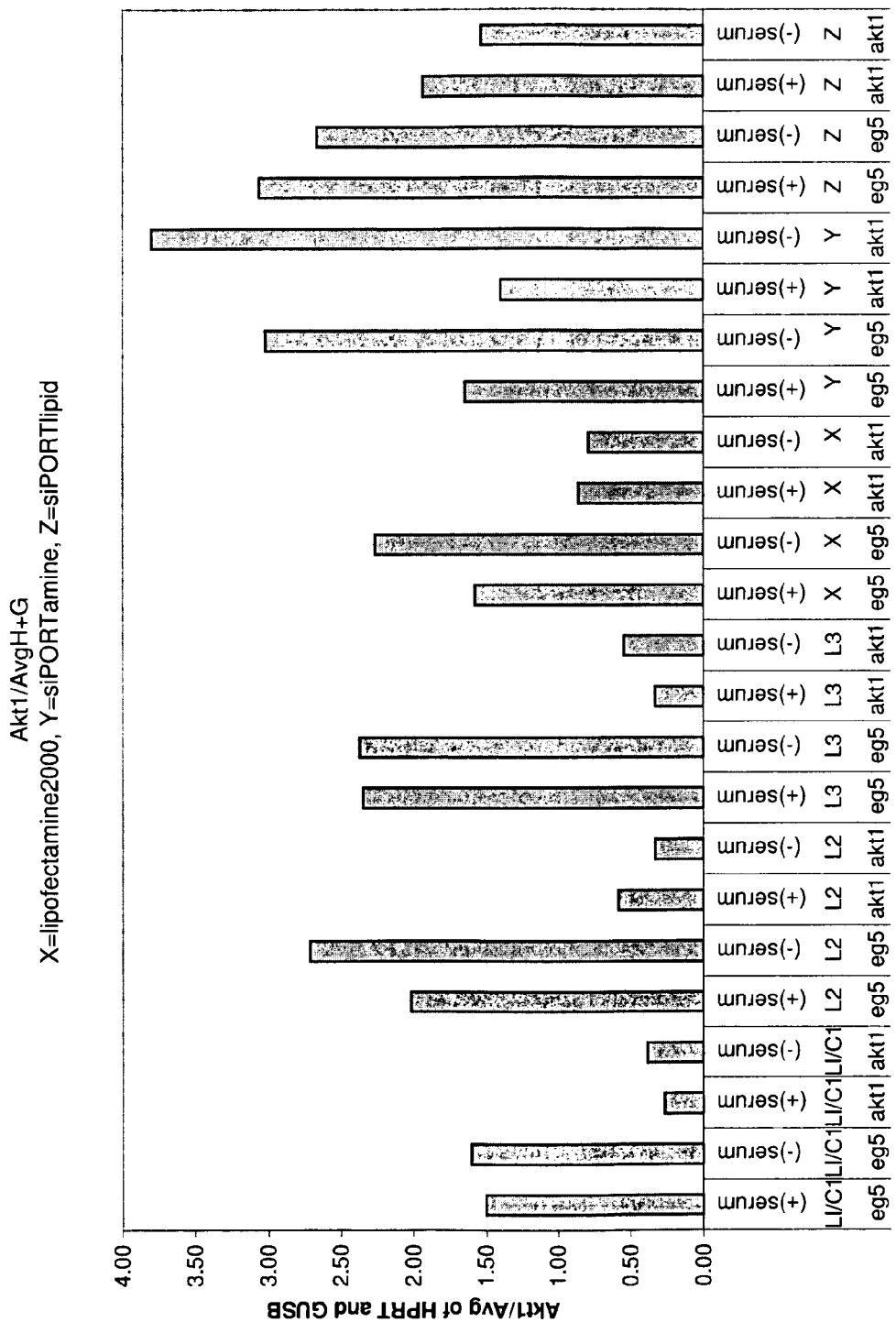
FIG. 2 is a plot showing loss of Akt1 expression when siRNA directed against Akt1 mRNA is transfected into MDA435 breast cancer cells using transfection compositions in accordance with the present invention.

FIG. 2 shows loss of Akt1 expression when siRNA directed against Akt1 mRNA is transfected into MDA435 breast cancer cells using transfection compositions prepared as described above. The effectiveness of three different lipitoid (L2, L3) or lipitoid/cholesteroid combination (L1/C1) vehicles with a series of commercially available delivery vehicles (X=lipofectamine2000, available from Invitrogen; Y=siPORTamine, available from Ambion; and Z=siPORTlipid, available from Ambion), all in the presence or absence of serum during transfection, is compared. The control was eg5 siRNA transfected into the cells at 100 nM concentration using the same vehicles and conditions. The eg5 siRNA was double-stranded, all RNA, with additional two TT nucleotide 3'-overhangs and phosphodiester links throughout and had a sequence corresponding to the DNA sequence AGAAACTAAATTACAACTTGTTA (SEQ ID NO:3). Total RNA was extracted using the Roche High Pure RNA Isolation Kit, according to manufacturer's protocols.

The results (normalized; average of HPRT and GUSB; message levels for Akt1 were normalized to the average of the levels of the housekeeping genes (HPRT and GUSB) to compensate for small variations in total RNA levels among samples) show that the transfection agents and compositions of the present invention are not substantially affected by the presence of absence of serum and that they are very effective in reducing expression of the target gene/mRNA.

Example 2

Loss of Luciferase Activity After siRNA Transfection

Figure 3:
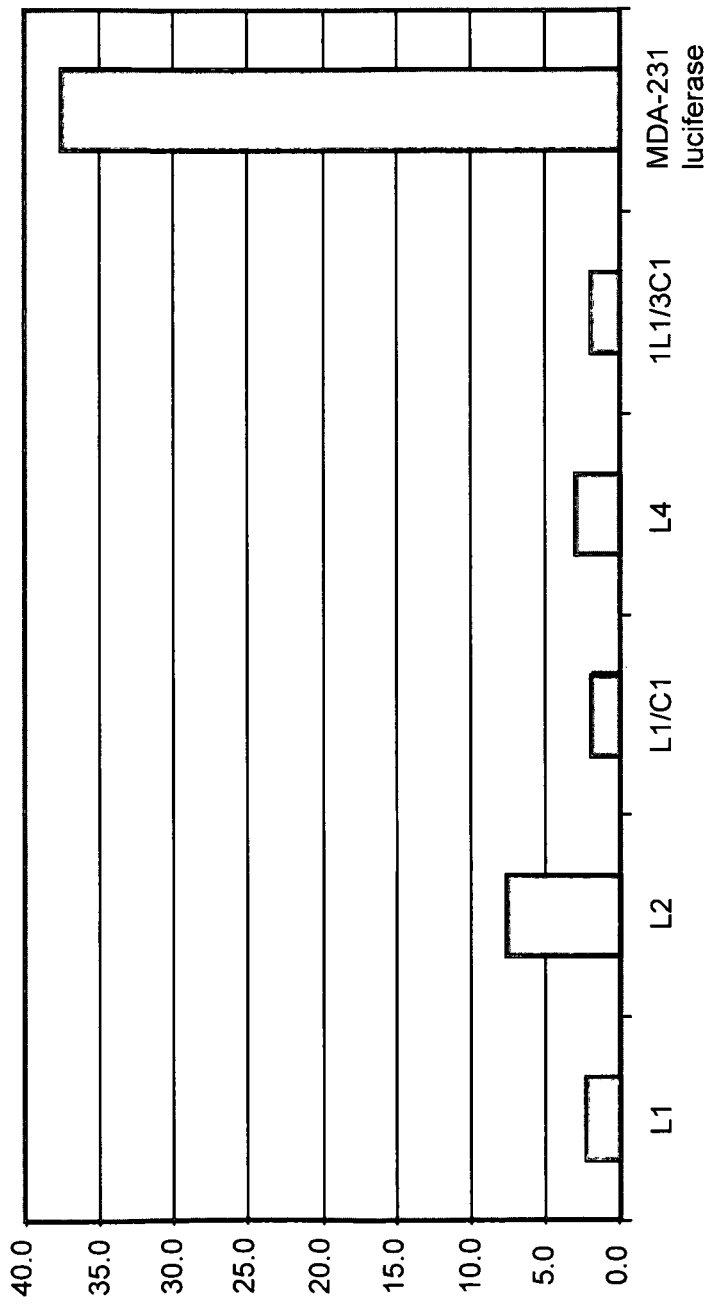
FIG. 3 is a plot showing luciferase activity in cells treated with transfection mixtures which were prepared using siRNA against firefly luciferase and several different delivery vehicles in accordance with the present invention.

Transfection mixtures were prepared using siRNA against firefly luciferase (CGUACGCGGAAUACUUCGA (SEQ ID No: 2); from Elbashir et al., Nature, 411, 494 (2001)) and several different delivery vehicles in accordance with the present invention as described herein (L1, L2, L1/C1, L4 1L1/3C1) substantially as described in Example 1. Luciferase activity was quantified with the Promega Dual-Luciferase Reporter Assay System according to package directions. As shown in FIG. 3, luciferase activity in MDA231 stably expressing luciferase was substantially reduced after transfection of an siRNA against luciferase. The control was a non-transfected cell line. This result provides further indication of the capability of compositions in accordance with the present invention for the effective delivery of siRNA to cells.

Example 3

Knockout of Akt1 Message in Cells Transfected with siRNA

Table 1 shows data for an experiment undertaken to compare the effectiveness of the knockout of Akt1 message in cells transfected with siRNAs by a composition incorporating a combination lipitoid/cholesteroid delivery vehicle in accordance with the present invention and using a commercially available transfection agent (Fugene6, available from Roche. HT1080 cells were transfected with 100 nM of two different siRNAs (siRNA directed against Akt1 messenger RNA having the sequence CAUAGUGAGGUUGCAUCUGGUG (SEQ ID No: 1) with two TT nucleotide 3'-overhangs and phosphodiester links throughout or with two 2' O-methyl UU (RNA) nucleotide 3'-overhangs and phosphodiester links throughout) using a composition incorporating a combination lipitoid/cholesteroid delivery vehicle (1L1/3C3) substantially according to the transfection mixture preparation and transfection procedures described in Example 1. Reduction in mRNA levels of about 69-83% was observed for compositions in accordance with the present invention. The results indicate that the compositions in accordance with the present invention are far more effective at Akt1 mRNA knockout than the commercial Fugene6 agent.

TABLE 1

| 100 nM | hu actin pp | akt1 pp | ratio to actin | % mRNA KO |
|---|---|---|---|---|
| 1:1 L1/C3 1:3 akt1#1 | 0.94 | 0.64 | 0.6795 | 69.3 |
| 1:1 L1/C3 1:3 akt1#3 | 0.89 | 0.48 | 0.5406 | 82.6 |

TABLE 1-continued

| 100 nM | hu actin pp | akt1 pp | ratio to actin | % mRNA KO |
|---|---|---|---|---|
| 1:5 Fugene6 akt1#1 | 0.40 | 0.66 | 1.6500 | 28.1 |
| 1:5 Fugene6 akt1#3 | 0.40 | 0.79 | 1.9628 | 9.0 |
| HT1080 wt | 0.80 | 1.97 | 2.4625 | 0.0 |

Although the foregoing invention has been described in some detail for purposes of clarity of understanding, it will be apparent that certain changes and modifications may be practiced within the scope of the appended claims. It should be noted that there are many alternative ways of implementing both the processes and compositions of the present invention. Accordingly, the present embodiments are to be considered as illustrative and not restrictive, and the invention is not to be limited to the details given herein, but may be modified within the scope and equivalents of the appended claims.

The contents of each of the patents, patent applications and journal articles cited above are hereby incorporated by reference herein and for all purposes as if fully set forth in their entireties.

---

---

What is claimed is:

1. A method of inhibiting expression of a target gene in a subject, the method comprising administering to the subject a composition comprising:

a small interfering ribonucleic acid (siRNA) in a pharmaceutically acceptable delivery vehicle, wherein the delivery vehicle comprises a lipid-cationic peptoid conjugate of the formula:

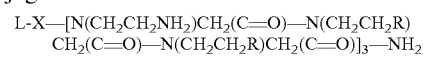

and positional isomers
where
L is selected from a non-sterol lipid moiety comprising at least one fatty alkyl or alkenyl chain between about 8 and 24 carbon atoms in length and a sterol moiety, wherein when L is a non-sterol lipid moiety, the peptoid conjugate is a lipitoid and when L is a sterol moiety, the peptoid conjugate is a cholesteroid;
each group R is independently selected from alkyl, aminoalkyl, and aralkyl, and
X is selected from the group consisting of a direct bond, an oligopeptide, a substantially linear alkyl chain from 2 to about 30 bonds in length, and a substantially linear chain from 2 to about 30 bonds in length consisting of alkyl bonds and one or more linkages selected from the group consisting of ester, amide, carbonate, carbamate, disulfide, peptide, and ether; wherein the delivery vehicle comprises a combination of lipitoid and cholesteroid peptoid conjugates; and
wherein one strand of the siRNA duplex has a nucleotide sequence comprised in an mRNA derived from the target gene.

2. The method of claim 1, wherein the lipitoid:cholesteroid ratio is about 5:1 to 1:5.

3. The method of claim 2, wherein the lipitoid:cholesteroid ratio is about 1:1 to 1:3.

4. The method of claim 3, wherein the lipitoid is DMPE (NaeNmpeNmpe)$_3$ and the cholesteroid is Chol-β-ala-(NaeNmpeNmpe)$_3$.

5. The method of claim 1, wherein the siRNA comprises the sequence represented by SEQ ID NO: 1 with two nucleotide 3'-overhangs and phosphodiester link throughout.

6. The method of claim 1, wherein the subject is a mammalian cell or cell line.

7. The method of claim 1, wherein the subject is a mammal.

8. The method of claim 7, wherein the subject is a human.

* * * * *

SEQUENCE LISTING

<160> NUMBER OF SEQ ID NOS: 3

<210> SEQ ID NO 1
<211> LENGTH: 22
<212> TYPE: RNA
<213> ORGANISM: Artificial
<220> FEATURE:
<223> OTHER INFORMATION: Synthetic

<400> SEQUENCE: 1
cauagugagg uugcaucugg ug                                              22

<210> SEQ ID NO 2
<211> LENGTH: 19
<212> TYPE: RNA
<213> ORGANISM: Artificial
<220> FEATURE:
<223> OTHER INFORMATION: Synthetic

<400> SEQUENCE: 2
cguacgcgga auacuucga                                                  19

<210> SEQ ID NO 3
<211> LENGTH: 23
<212> TYPE: DNA
<213> ORGANISM: Artificial
<220> FEATURE:
<223> OTHER INFORMATION: Synthetic

<400> SEQUENCE: 3
agaaactaaa ttacaacttg tta                                             23